United States Patent [19]

Gazzaniga et al.

[11] Patent Number: 4,834,966
[45] Date of Patent: * May 30, 1989

[54] PHARMACEUTICAL COMPOSITION WITH ANALGESIC ACTIVITY

[75] Inventors: Annibale Gazzaniga, Rescaldina, Italy; Valter Gianesello, Origlio; Federico Stroppolo, Pregassona; Luigi Viganó, Lugano, all of Switzerland

[73] Assignee: Zambon S.p.A., Milan, Italy

[ * ] Notice: The portion of the term of this patent subsequent to Aug. 25, 2004 has been disclaimed.

[21] Appl. No.: 76,547

[22] Filed: Jul. 22, 1987

[30] Foreign Application Priority Data

Aug. 1, 1986 [IT] Italy .................. 21358 A/86

[51] Int. Cl.$^4$ ............................... A61K 9/00
[52] U.S. Cl. ................................. 424/43; 424/717; 514/565; 514/570

[58] Field of Search ............... 514/565, 570; 424/127, 424/43

[56] References Cited

U.S. PATENT DOCUMENTS

| | | | |
|---|---|---|---|
| 4,279,926 | 7/1981 | Brazzese et al. | 514/555 |
| 4,569,937 | 2/1986 | Baker et al. | 514/557 |
| 4,593,044 | 6/1986 | Metz | 514/557 |
| 4,689,218 | 8/1987 | Gazzaniga et al. | 514/557 |

*Primary Examiner*—Paul Lieberman
*Assistant Examiner*—Willie J. Thompson
*Attorney, Agent, or Firm*—Stevens, Davis, Miller & Mosher

[57] ABSTRACT

A pharmaceutical composition consisting of:
  Ibuprofen: 33–46% w/w
  L-arginine: 34–51% w/w
  Sodium bicarbonate: 9–29% w/w
is useful for preparing soluble granulate pharmaceutical preparations.

8 Claims, No Drawings

PHARMACEUTICAL COMPOSITION WITH ANALGESIC ACTIVITY

The present invention relates to a pharmaceutical composition with analgesic activity and, more particularly, it relates to a pharmaceutical composition for oral use containing Ibuprofen as active ingredient.

Ibuprofen [2-(4-isobutyl-phenyl)-propionic acid] is a known drug (Merck Index, 10th Edition, No. 4797) used in therapy for its analgesic and anti-inflammatory properties.

This drug is administered in therapy mainly in the form of tablets, sugar coated tablets or suppositories and produces, likewise the other non-steroidal anti-inflammatory compounds, gastric irritation due both to a systemic action and to a simple direct action on the gastro-intestinal mucosa.

As far as Ibuprofen is concerned the systemic action on the gastric mucosa is of little importance.

By administering the drug in solid pharmaceutical preparations such as tablets or sugar coated tablets there is the appearance of a possible irritation because of the direct action on the mucosa. By administering the drug in the form of an aqueous suspension the irritating damages appear also on the mucosa of the oral cavity; furthermore the palatability is not acceptable because of the very unpleasant taste of the drug.

On the other hand also the administration for suppository route produces local irritation.

In order to overcome the drawbacks hereabove described it could be useful to have available an aqueous solution of Ibuprofen. However the drug has a very little solubility in water, many of its salts are relatively little soluble and are, therefore, not suitable for use in a soluble pharmaceutical preparation. Ibuprofen sodium salt is one of few salts with a good solubility in water but it is not very suitable for an oral preparation because it gives solutions having a pH which produces gastrointestinal damages.

We have now surprisingly found a composition containing Ibuprofen and which can be used for the preparation of granulates having a complete solubility in water.

These compositions allow, then, to prepare in a rapid and efficacious way aqueous solutions of Ibuprofen at the moment of use. The composition object of the present invention consists of (percentage in weight):

"Ibuprofen": 33–46%
L-arginine: 34–51%
Sodium bicarbonate: 9–29%
the total being 100%.

The molar ratio between arginine and Ibuprofen must be between 1.1 and 1.5, preferably 1.2.

The weight ratio between sodium bicarbonate and Ibuprofen is between 0.25 and 0.75, preferably 0.5.

Some specific examples of the compositions according to the present invention are reported in the following table 1.

Table 1

Compositions according to the present invention (percentage in weight)

|   | Ibuprofen | L-arginine | Sodium bicarbonate | L-arginine/ Ibuprofen (molar ratio) | Sodium bicarbonate/ Ibuprofen (weight ratio) |
|---|---|---|---|---|---|
| a | 44.18 | 44.77 | 11.05 | 1.2 | 0.25 |
| b | 39.76 | 40.36 | 19.88 | 1.2 | 0.5 |
| c | 36.19 | 36.67 | 27.14 | 1.2 | 0.75 |
| d | 45.98 | 42.53 | 11.49 | 1.1 | 0.25 |
| e | 41.24 | 38.14 | 20.62 | 1.1 | 0.5 |
| f | 37.38 | 34.58 | 28.04 | 1.1 | 0.75 |
| g | 39.74 | 50.33 | 9.93 | 1.5 | 0.25 |
| h | 36.17 | 45.75 | 18.08 | 1.5 | 0.5 |
| i | 33.17 | 41.96 | 24.88 | 1.5 | 0.75 |

The complete solubility in water of the compositions object of the present invention allows an easy administration and a very good tolerability on the level of both oral and gastric mucosa.

It is worth noting that the use of the arginine salt of Ibuprofen (U.S. Pat. No. 4,279,926—SPA) is not suitable in the preparation of granulates because it does not result in a complete solubilization of the Ibuprofen (see example 13).

Besides, surprisingly, these compositions show a high increase of the absorption rate of Ibuprofen, in comparison with known pharmaceutical compositions, and consequently there is a faster appearance of the analgesic effect. This effect lasts a period of time substantially as long as the period observed in the case of administration of a tablet of Ibuprofen and, consequently, the analgesic action has a longer duration.

The use of the compositions according to the present invention causes also a reduced change in the individual variations of the absorption kinetics.

With the compositions object of the present invention it is possible to prepare granulates by adding thereto the usual excipients for the granulation and other excipients such as sweeteners, artificial sweeteners, flavouring agents and optionally dyes.

The pharmaceutical compositions in the form of granulates prepared from the compositions object of the present invention form a further object of the invention.

The above preparations in the form of a granulate do not change the solubility in water of the compositions from which they are obtained.

Some specific examples of the pharmaceutical preparations according to the present invention are the following (percentage in weight):

(a)

"Ibuprofen": 6.67%
L-arginine: 6.17%
Sodium bicarbonate: 3.33%
Sweeteners: 1.17%
Flavouring agents: 3.33%
Other excipients: q.s. to 100%

(b)

"Ibuprofen": 6.67%
L-arginine: 6.77%
Sodium bicarbonate: 1.67%
Sweeteners: 1.17%
Flavouring agents: 3.33%
Other excipients: q.s. to 100%

(c)

"Ibuprofen": 6.67%
L-arginine: 8.43%

Sodium bicarbonate: 5.00%
Sweeteners: 1.17%
Flavouring agents: 3.33%
Other excipients: q.s. to 100%

(d)

"Ibuprofen": 13.33%
L-arginine: 13.53%
Sodium bicarbonate: 6.67%
Sweeteners: 1.50%
Flavouring agents: 4.83%
Other excipients: q.s. to 100%

(e)

"Ibuprofen": 13.33%
L-arginine: 16.87%
Sodium bicarbonate: 6.67%
Sweeteners: 1.50%
Flavouring agents: 4.83%
Other excipients: q.s. to 100%

(f)

"Ibuprofen": 13.33%
L-arginine: 13.53%
Sodium bicarbonate: 10.00%
Sweeteners: 1.50%
Flavouring agents: 4.83%
Other excipients: q.s. to 100%

(g)

"Ibuprofen": 20.00%
L-arginine: 25.30%
Sodium bicarbonate: 10.00%
Sweeteners: 1.83%
Flavouring agents: 5.00%
Other excipients: q.s. to 100%

(h)

"Ibuprofen": 20.00%
L-arginine: 20.30%
Sodium bicarbonate: 5.00%
Sweeteners: 1.83%
Flavouring agents: 5.00%
Other excipients: q.s. to 100%

The pharmaceutical preparations object of the present invention are prepared in the form of a granulate according to conventional techniques and are distributed in bags.

Each bag contains from 1200 mg to 3000 mg of granulate and contains an amount of Ibuprofen corresponding to a dosage of 100-200-400 or 600 mg.

Among the used excipients examples of sweeteners are saccharose, fructose, sorbitol, lactose and mixtures thereof, which may act also as diluents.

Examples of artificial sweeteners are saccharin, cyclamates, aspartame and mixture thereof.

Pharmaceutically acceptable dyes can also be optionally used. The increase of the absorption rate was estimated by the evaluation of plasma concentrations during the time after administering a solution of Ibuprofen obtained by dissolving in water a granulate according to the present invention containing 200 mg active ingredient (see examples 11 and 12).

The analysis of plasma concentration/time curve shows a remarkable anticipation of the peak time and an increase of the maximum plasma concentration.

In particular the peak time changes from the value of 1.5-2 hours for commercial tablets containing Ibuprofen to the value of only about 15 minutes in case of administration of the preparation according to the present invention.

Contemporaneously the other pharmacokinetic parameters (AUC, distribution volume, total clearance) are substantially the same (see example 12).

Among these (pharmacokinetic parameters) the most important one is the not significant difference from the values of half time reported in literature (Kenneth S. Albert, Charlene M. Gernaat, The American Journal of Medicine, 13-7-1984, pag. 40).

The analgesic effect of the preparations object of the present invention ends after a number of hours from the administration substantially equal to that of commercially available solid pharmaceutical preparations.

Consequently, since the analgesic effect begins earlier, the compositions object of the present invention result in a longer duration of such effect.

The peculiarity of the present invention is, therefore, the fact that by using the above described compositions it is possible to obtain the desired therapeutic effect within few minutes and with a longer total duration.

It is clear how such features are advantageous in a preparation with analgesic effect.

In order to better illustrate the present invention the following examples are now given.

EXAMPLE 1

A granulate having the composition
"Ibuprofen": 80 g
L-arginine: 74 g
Sodium bicarbonate: 40 g
is prepared according to the following procedure.

The powders are sieved separately through a net (1.07 mm mesh) and then put in a granulator and dry mixed for 10 minutes.

The mixture is granulated with water at 90° C. After partial drying the wet granulate is placed into a static bed dryer.

At the end of the drying the granulate is passed by a vibrating screen through a net with 0.8 mm mesh.

This granulate, after adding saccharose (952 g), sodium saccharin (6 g), aspartame (8 g), mint flavor (40 g) and further mixing, is distributed in 400 bags of 3000 mg each.

EXAMPLE 2

A granulate having the composition
"Ibuprofen": 80 g
L-arginine: 74 g
Sodium bicarbonate: 40 g
Saccharose: 952 g
Sodium saccharin: 6 g
Aspartame: 9 g
Mint flavour: 40 g
is prepared according to the following procedure.

Ibuprofen and L-arginine are sieved through a net (1.07 mm mesh) and then put in a granulator. They are dry mixed for 10 minutes and then granulated with water at 90° C. After partial drying the wet granulate is transferred to a static bed dryer. At the end of the drying the granulate is passed by a vibrating screen through a net with 0.8 mm mesh. Sodium bicarbonate and the remaining excipients are added to this granulate after having been sieved on net with 1.07 mm mesh. The whole is dry mixed for 30 minutes.

The so obtained granulate is distributed in 400 bags of 3000 mg each.

EXAMPLE 3

By operating in a way similar to that described in example 2 a granulate having the following compositions is prepared:
 "Ibuprofen": 160 g
 L-arginine: 148 g
 Sodium bicarbonate: 80 g
 Saccharose: 736 g
 Sodium saccharin: 8 g
 Aspartame: 10 g
 Mint flavour: 40 g
 Vanilla flavour: 18 g The so obtained granulate is distributed in 400 bags of 3000 mg weight each.

EXAMPLE 4

By operating in a way similar to that described in example 2 a granulate having the following composition is prepared:
 "Ibuprofen": 240 g
 L-arginine: 222 g
 Sodium bicarbonate: 120 g
 Saccharose: 536 g
 Sodium saccharin: 10 g
 Aspartame: 12 g
 Mint flavour: 54 g
 Anise flavour: 6 g The so obtained granulate is distributed in 400 bags of 3000 mg weight each.

EXAMPLE 5

By operating in a way similar to that described in example 2 a granulate having the following composition is prepared:
 "Ibuprofen": 80 g
 L-arginine: 74 g
 Sodium bicarbonate: 40 g
 Sorbitol: 228 g
 Sodium saccharin: 6 g
 Aspartame: 12 g
 Mint flavour: 40 g The so obtained granulate is distributed in 400 bags of 1200 mg weight each.

EXAMPLE 6

By operating in a way similar to that described in example 2 a granulate having the following composition is prepared:
 "Ibuprofen": 80 g
 L-arginine: 81.2 g
 Sodium bicarbonate: 40 g
 Saccharose: 944.8 g
 Sodium saccharin: 6 g
 Aspartame: 8 g
 Mint flavor: 40 g The so obtained granulate is distributed in 400 bags of 3000 mg weight each.

EXAMPLE 7

By operating in a way similar to that described in example 2 a granulate having the following composition is prepared:
 "Ibuprofen": 80 g
 L-arginine: 101.2 g
 Sodium bicarbonate: 40 g
 Saccharose: 924.8 g
 Sodium saccharin: 6 g
 Aspartame: 8 g
 Mint flavor: 40 g The so obtained granulate is distributed in 400 bags of 3000 mg weight each.

EXAMPLE 8

By operating in a way similar to that described in example 2 a granulate having the following composition is prepared:
 "Ibuprofen": 80 g
 L-arginine: 74 g
 Sodium bicarbonate: 20 g
 Saccharose: 970 g
 Sodium saccharin: 6 g
 Aspartame: 8 g
 Mint flavour: 30 g
 Anise flavour: 12 g The so obtained granulate is distributed in 400 bags of 3000 mg weight each.

EXAMPLE 9

By operating in a way similar to that described in example 2 a granulate having the following composition is prepared:
 "Ibuprofen": 80 g
 L-arginine: 74 g
 Sodium bicarbonate: 60 g
 Saccharose: 932 g
 Sodium saccharin: 6 g
 Aspartame: 8 g
 Mint flavor: 40 g The so obtained granulate is distributed in 400 bags of 3000 mg weight each.

EXAMPLE 10

By operating in a way similar to that described in example 2 a granulate having the following composition is prepared:
 "Ibuprofen": 40 g
 L-arginine: 37 g
 Sodium bicarbonate: 20 g
 Saccharose: 346 g
 Sodium saccharin: 6 g
 Aspartame: 11 g
 Mint flavour: 20 g The so obtained granulate is distributed in 400 bags of 1200 mg weight each.

EXAMPLE 11

Aqueous solutions of the granulate described in example 2, containing 200 mg of Ibuprofen, were administered with a single oral dose to 10 apparently healthy voluntary patients aged 37.3 years on the average.

Drawings of blood were made before the administration and after 15, 10, 60, 240 and 480 minutes from the administration. The analytical determination of Ibuprofen in the blood samples was carried out following the HPLC method hereinafter described. Chromatographic conditions: Chromatograph: JASCO BIP-1 with UV detector UVIDEC 100-V Mobil phase: $CH_3CN$: tetrabutylammonium hydroxide 0.005M (corrected to pH 7 with $H_3PO_4$ (38:62)
 Flow: 2 ml/min
 Wavelenght: 225 nm
 Internal standard: a solution in acetonitrile of ethyl p-hydroxybenzoate 0.0048M 5 μl of internal standard were added to 0.1 ml of blood. The whole was mixed and 1 ml of mobil phase was added to it.

It was extracted and allowed to rest for 30 minutes.

It was centrifuged at 4000 rpm and filtered through a 0.45 um filter.

20 μl of the filtrate were injected into the chromatograph.

The retention times were:
Internal standard: $R_t = 4.5$ minutes
Ibuprofen: $R_t = 5.5$ minutes The obtained results are reported in the following table.

Table 2

Mean plasma concentration of Ibuprofen after oral treatment with solution of a granulate obtained by the compositions object of the present invention. Administered dose: 200 mg of active ingredient.

| minutes after treatment | mean plasma concentration of Ibuprofen (μg/ml) |
| --- | --- |
| 15 | 29.2 |
| 30 | 22.5 |
| 60 | 16.7 |
| 240 | 4.8 |
| 480 | 1.2 |

EXAMPLE 12

The experiment described in example 11 was repeated in order to compare the increase of the absorption rate of the compositions according to the present invention in comparison with Ibuprofen commercial tablets.

Aqueous solutions (100 ml) of the granulate described in example 2 containing 200 mg of Ibuprofen (treatment A) and Ibuprofen commercial tablets containing the same amount of active ingredient (treatment B) were administered with a single oral dose to 12 subjects aged 33.5 years on the average.

Each subject was apparently healthy, in particular as far as the renal, hepatic and hematopoietic function are concerned.

For the experiment a "cross-over" design was adopted: each subject received both preparations in two treatment sessions carried out 2 weeks apart, randomizing the order of administration.

During each of the two sessions, basal sample of venous blood were drawn (in the morning) from each fasting subject, prior to oral administration of the preparation A or B. Further venous blood samples were also collected 5, 10, 15, 30, 60, 120, 240 and 360 minutes after treatment.

The analytical determination of Ibuprofen in the blood samples was carried out following the HPLC method described in example 11.

Table 3

Mean plasma concentration of Ibuprofen after oral treatment with solution of granulates according to the present invention (treatment A) and after oral treatment with commercial Ibuprofen tablets (treatment B). Administered dose: 200 mg of active ingredient.

| Treatment | Ibuprofen plasma concentration (μg/ml) time after treatment (minutes) | | | | | | | |
| --- | --- | --- | --- | --- | --- | --- | --- | --- |
| | 5 | 10 | 15 | 30 | 60 | 120 | 240 | 360 |
| A | 11.9 | 21.0 | 23.3 | 21.5 | 16.7 | 11.0 | 5.4 | 2.9 |
| B | 0.9 | 0.6 | 1.8 | 8.1 | 12.6 | 12.3 | 7.9 | 4.5 |

Bioavailability parameters:

The following parameters were calculated and evaluated.

The area under the curve of Ibuprofen plasma concentration from time "zero" to time 360 minutes (AUC obs = $AUC_{0 \to 360}$), expressed as ug.min.ml$^{-1}$, was calculated following the "trapezoidal rule" method (Gibaldi M. and Perrier D., "Pharmacokinetics", pages 293-296, Mercel Dekker Inc., New York 1975).

The area under curve of Ibuprofen plasma concentration from time "zero" to "infinite" (AUC tot) was calculated by the following formula:

$$AUC_{0 \to 360} + AUC_{360 \to \infty}$$

where $$AUC_{360 \to \infty} = \text{conc. } 360 \text{ min}/Ke^{(a)}$$

(a) Ke = elimination constant.

The mean peak time expressed in minutes was obtained by averaging the individual peak times.

The mean plasma peak (C max) expressed as μg/ml was calculated by averaging the single peak values of the concentrations.

Lag time (minutes): is the delay between the drug administration and the beginning of absorption.

The values of the above specified bioavailability parameters are reported in the following table.

Table 4

Pharmacokinetic parameters obtained after oral treatment with solution of Ibuprofen granulates (treatment A) and with Ibuprofen commercial tablets (treatment B). Administered dose: 200 mg of active ingredient.

| Analyzed parameter | Treatment A | Treatment B |
| --- | --- | --- |
| AUC obs (μg · min · ml$^{-1}$) | 3413.2 | 2094.2 |
| AUC tot (μg · min · ml$^{-1}$) | 4020.6 | 4094.5 |
| Peak time (min.) | 16.9 | 90 |
| Plasma concentration C max (μg/ml) | 25.7 | 16.3 |
| Lag time (min.) | 1.6 | 8.12 |

EXAMPLE 13

By operating according to the procedure described in example 2, a granulate was prepared having the following composition (Reference B)

2-(4-isobutyl-phenyl)-propionate of arginine(*): 1106.7 mg
Sodium bicarbonate: 300.0 mg
Saccharose: 1388.3 mg
Sodium saccharin: 25.0 mg
Aspartame: 30.0 mg
Mint flavour: 135.0 mg
Anise flavour: 15.0 mg (*) Salt of Ibuprofen with Arginine corresponding to 600 mg of "Ibuprofen"

The granulate corresponding to 600 mg of Ibuprofen (Composition A) prepared as described in example 4 and Reference B were added to 100 ml of water at the temperature of 20° C.

After dissolution of the granulates the presence and the amount of precipitate (Ibuprofen) were evaluated.

Composition A gave a clear solution and no precipitate was observed.

For reference B the formation of plate, insoluble crystals of Ibuprofen was observed on the surface of the water.

The presence of undissolved Ibuprofen makes unacceptable the preparation both for the taste and for the local tolerability.

What we claim is:

1. A pharmaceutical composition with analgesic activity, suitable to prepare pharmaceutical preparations with a complete solubility in water, consisting of:
   "Ibuprofen": 33–46% w/w
   L-arginine: 34–51% w/w
   Sodium bicarbonate: 9–29% w/w
the whole being 100%, the molar ratio between L-arginine and Ibuprofen being between 1.1 and 1.5 and the weight ratio between sodium bicarbonate and "Ibuprofen" being between 0.25 and 0.75.

2. A pharmaceutical composition according to claim 1 in which the molar ratio between L-arginine and "Ibuprofen" is 1.2.

3. A pharmaceutical composition according to claim 1 in which the weight ratio between sodium bicarbonate and "Ibuprofen" is 0.5.

4. A pharmaceutical preparation in the form of a granulate containing a composition according to claim 1 and excipients for pharmaceutical use suitable to prepare water soluble granular preparations.

5. A pharmaceutical preparation in the form of a granulate containing each dose a composition according to claim 1 containing an amount of "Ibuprofen" corresponding to 100 mg, 200 mg, 400 mg or 600 mg.

6. A pharmaceutical preparation according to claim 4 in which the excipients suitable to prepare water soluble granular preparations are selected among sweeteners, flavouring agents and optionally pharmaceutically acceptable dyes.

7. A pharmaceutical preparation according to claim 6 in which the sweetener is selected among saccharose, fructose, sorbitol, lactose and mixtures thereof.

8. A pharmaceutical preparation according to claim 6 in which the sweetener is selected among saccharin, cyclamates, aspartame and mixtures thereof.

* * * * *